United States Patent
Hameed (10) Patent No.: US 8,951,226 B2
(45) Date of Patent: Feb. 10, 2015

(54) MEDIASTINOSCOPY ACCESS, SAMPLING, AND VISUALIZATION KIT FEATURING TOROIDAL BALLOONS AND EXOTRACHEAL METHOD OF USING

(75) Inventor: Salmaan Hameed, San Jose, CA (US)

(73) Assignee: Chest Innovations, Inc., Pleasanton, CA (US)

( * ) Notice: Subject to any disclaimer, the term of this patent is extended or adjusted under 35 U.S.C. 154(b) by 188 days.

(21) Appl. No.: 12/544,681

(22) Filed: Aug. 20, 2009

(65) Prior Publication Data

US 2010/0049162 A1    Feb. 25, 2010

Related U.S. Application Data

(60) Provisional application No. 61/090,510, filed on Aug. 20, 2008, provisional application No. 61/148,916, filed on Jan. 30, 2009.

(51) Int. Cl.

| | |
|---|---|
| *A61M 29/00* | (2006.01) |
| *A61M 29/02* | (2006.01) |
| *A61M 25/10* | (2013.01) |
| *A61B 17/02* | (2006.01) |
| *A61B 1/00* | (2006.01) |
| *A61B 1/313* | (2006.01) |
| *A61B 10/06* | (2006.01) |
| *A61B 18/14* | (2006.01) |
| *A61B 19/04* | (2006.01) |

(Continued)

(52) U.S. Cl.
CPC ......... *A61B 17/0218* (2013.01); *A61B 1/00082* (2013.01); *A61B 1/313* (2013.01); *A61B 10/06* (2013.01); *A61B 18/1445* (2013.01); *A61B 19/04* (2013.01); *A61B 19/5212* (2013.01); *A61B 2017/00544* (2013.01); *A61B 2017/00557* (2013.01); *A61B 2017/00858* (2013.01); *A61B 2017/22055* (2013.01); *A61B 2017/22068* (2013.01); *A61B 2017/22069* (2013.01); *A61B 2017/2905* (2013.01); *A61M 29/00* (2013.01)
USPC ............ 604/101.05; 128/200.24; 128/207.15; 600/202; 600/204; 600/207; 600/547; 600/587; 604/198; 606/119; 606/129; 606/191; 606/192; 606/193; 606/197

(58) Field of Classification Search
USPC ......... 128/200.24, 207.15, 547, 587, 59, 899; 600/202, 204, 207, 547, 562, 587, 197; 604/101.05, 198; 606/119, 129, 606/191–193, 197
See application file for complete search history.

(56) References Cited

U.S. PATENT DOCUMENTS

| | | |
|---|---|---|
| 3,730,186 A | 5/1973 | Edmunds, Jr. et al. |
| 4,183,102 A * | 1/1980 | Guiset .......................... 623/1.25 |

(Continued)

*Primary Examiner* — Sean Dougherty (57) ABSTRACT

The present invention provides various systems, a kit, and a method for accessing, sampling within, and visualization of areas within the mediastinal cavity for assisting a surgeon in performing a mediastinoscopy procedure. The access system includes one or more preferably toroidal balloons that can be expanded to dilate and protect the inner walls of a bodily conduit. Instruments pass through hollow spaces within the expanded toroidal balloons. The proximally positioned balloons are expanded first and the unexpanded balloons to be positioned distally are passed through them and subsequently expanded. The sampling system includes an instrument with a rounded head having two or more jaws and a slit therein at the distal end of an elongated tubular body. The visualization system includes a 360° camera that can be positioned from proximal to distal a target site and can also do a U-turn about its axis of extension.

11 Claims, 5 Drawing Sheets

(51) Int. Cl.
*A61B 19/00* (2006.01)
*A61B 17/00* (2006.01)
*A61B 17/22* (2006.01)
*A61B 17/29* (2006.01)

(56) References Cited

U.S. PATENT DOCUMENTS

| | | | |
|---|---|---|---|
| 4,921,478 A * | 5/1990 | Solano et al. | 604/509 |
| 4,984,564 A * | 1/1991 | Yuen | 600/207 |
| 5,413,558 A * | 5/1995 | Paradis | 604/101.05 |
| 5,423,742 A * | 6/1995 | Theron | 604/28 |
| 5,470,314 A * | 11/1995 | Walinsky | 604/103.11 |
| 5,656,013 A * | 8/1997 | Yoon | 600/207 |
| 5,823,947 A * | 10/1998 | Yoon et al. | 600/207 |
| 5,941,819 A | 8/1999 | Chin | |
| 6,053,891 A | 4/2000 | DeCampli | |
| 6,120,437 A * | 9/2000 | Yoon et al. | 600/204 |
| 6,146,370 A * | 11/2000 | Barbut | 604/500 |
| 6,206,868 B1 * | 3/2001 | Parodi | 604/500 |
| 6,533,800 B1 * | 3/2003 | Barbut | 606/194 |
| 6,595,980 B1 * | 7/2003 | Barbut | 604/509 |
| 6,695,864 B2 * | 2/2004 | Macoviak et al. | 606/200 |
| 6,852,108 B2 | 2/2005 | Barry et al. | |
| 6,887,227 B1 * | 5/2005 | Barbut | 604/500 |
| 6,913,610 B2 * | 7/2005 | Nakao | 606/192 |
| 6,945,957 B2 * | 9/2005 | Freyman | 604/96.01 |
| 7,122,003 B2 * | 10/2006 | Nakao | 600/204 |
| 7,232,414 B2 | 6/2007 | Gonzales | |
| 7,244,242 B2 * | 7/2007 | Freyman | 604/96.01 |
| 7,335,192 B2 | 2/2008 | Keren et al. | |
| 7,374,561 B2 | 5/2008 | Barbut | |
| 7,396,329 B2 | 7/2008 | Nakao | |
| 7,452,352 B2 | 11/2008 | Barbut | |
| 7,458,980 B2 | 12/2008 | Barbut | |
| 7,473,530 B2 | 1/2009 | Huttemann | |
| 7,780,627 B2 * | 8/2010 | Freyman | 604/96.01 |
| 8,460,240 B2 * | 6/2013 | Towler | 604/103.07 |
| 2002/0010411 A1 * | 1/2002 | Macoviak et al. | 604/8 |
| 2002/0029006 A1 * | 3/2002 | Turturro et al. | 600/562 |
| 2003/0225433 A1 * | 12/2003 | Nakao | 606/191 |
| 2005/0154298 A1 * | 7/2005 | Barbut | 600/435 |
| 2005/0209580 A1 * | 9/2005 | Freyman | 604/509 |
| 2008/0086083 A1 * | 4/2008 | Towler | 604/103.06 |
| 2008/0221552 A1 * | 9/2008 | Leonard | 604/509 |
| 2009/0054922 A1 * | 2/2009 | Broker | 606/194 |
| 2009/0270964 A1 * | 10/2009 | Huetter et al. | 623/1.11 |
| 2010/0228192 A1 * | 9/2010 | O'Dea et al. | 604/104 |

* cited by examiner

MEDIASTINOSCOPY ACCESS, SAMPLING, AND VISUALIZATION KIT FEATURING TOROIDAL BALLOONS AND EXOTRACHEAL METHOD OF USING

BACKGROUND OF THE INVENTION

1. Field of the Invention

The present invention relates to medical devices designed to assist a physician in performing a mediastinoscopy procedure. More specifically, the invention provides a kit of various systems that work together to improve access, sampling, and visualization during the procedure. Most specifically, the invention relates to inflatable devices for dilating a lumen or cavity in order to prepare a target site, including a mediastinal region, for access by instruments.

2. Description of the Related Art

The term mediastinoscopy refers to an examination of the mediastinum through an incision above and behind the sternum (breastbone) with a suprasternal incision. The mediastinum is the partition separating the right and left thoracic cavities. It is formed from the two inner pleural walls and includes all of the viscera of the thorax except for the lungs. More specifically, the organs in the mediastinal region include the heart and its vessels, the lymph nodes, the trachea, the esophagus, and the thymus. The individual devices and comprehensive self-sufficient kit of the present invention are designed to facilitate the process of inspecting, biopsying, and treating the mediastinum and surrounding areas to observe, detect, and ameliorate cancer or other abnormal tissue conditions.

A mediastinoscopy is an early stage or first step procedure performed in patients suspected of having lung cancer prior to thoracic surgery or other advanced therapy. Typically, a mediastinoscopy is performed to sample or biopsy lymph nodes in the paratracheal and parabroncial regions for cancer staging. Mediastinoscopy is also used to detect lymphoma, Hodgkin's disease, sarcoidosis (a chronic disease of unknown cause characterized by granulomatous tubercles or lesions of the lymph nodes, lungs, and other structures), and other conditions.

Problems with conventional devices and approaches for mediastinoscopy are numerous. First, traditional access is through a percutaneous incision in the neck. This leaves a visibly obvious, slow-healing, and painful scar through the many sensitive muscles and nerves in the neck. Second, visualization is typically poor and even with the assistance of an endoscopic monitor and ultrasound, skilled surgeons have difficulty accessing nodes and assessing whether a node, nodule, or tumor they are about to resect or sever from surrounding tissue is in fact the intended target. Additionally, operating within dark narrow working spaces increases the risk that the surgeon will inadvertently injure or at least aggravate critical vulnerable structures (including coronary arteries, valves, the heart itself) or puncture a lung in the same general region as the nodes while trying to reach the nodes. Third, the elongated instruments presently available require reaching out to grasp nodes, cutting, and dangling the severed, potentially abnormal tissue within the cavity prior to removal. This method risks dropping the sample prior to removal and can cause scattering of malignant particulate material for redistribution in the body amongst healthy tissue.

U.S. Pat. No. 7,232,414 (from hereon "USP '414") entitled "System and method for capturing body tissue samples" by Hugo X. Gonzalez and assigned to Spiration, Inc. (Redmond, Wash.) discloses a system and method that reduces the risk of scattering abnormal cells during sampling. The system includes a bag means with an open end for receiving a sample and a vacuum suction tube for first pulling a portion of tissue into a protected cove prior to resecting and then for drawing the resected portion to a proximal end of the instrument for removal, collection, and histological analysis. This system and method however, do not address improving the initial visualization of and access to nodes in crevices or at angles out of the direct trajectory through which an instrument has been inserted.

U.S. Pat. No. 6,852,108 (from hereon "USP '108") entitled "Apparatus and method for resecting and removing selected body tissue from a site inside a patient" by Robert Lawrence Barry, et al. and also assigned to Spiration, Inc. also focuses on reducing the chance of scattering material while resecting a sample. USP '108 elaborates to a greater extent than USP '414 on the position and design of an electrode used for resecting and on a collection chamber at the proximal end of the instrument with a plurality of compartments for indexing samples and preventing cross-contamination. For example, FIG. 9 shows electrode 100 housed within the protected interior of resection lumen 115 into which the vacuum draw 105 directs a portion of tissue (left upper paratracheal node 711) prior to it being contacted by the electrode. The blade electrode may be made extendable as shown in FIG. 10. Alternatively, it may be designed in the shape of a lasso 120 to form a loop 122 as shown in FIG. 13. In any case, all of the action takes place inside the resection lumen 115 of the tubular member 92 (FIGS. 7-15 are illustrative). The tubular member is inserted percutaneously through the skin after "making an incision at the sternal notch 27 just above the sternum 25" and it is placed "through the incision and between the trachea 28 and the top of the sternum 25" (7:19-34 and FIG. 6). There is no mention of using natural orifices to deliver the tubular member. There is also no disclosure of dilation elements or balloons to protect the trachea, sternum, etc. from agitation by the tubular member. A built-in improved viewing component is not taught as part of the device (7:31-34).

U.S. Pat. No. 5,941,819 (from hereon "USP '819") entitled "Apparatus for creating a mediastinal working space" by Albert K. Chin and assigned to Origin Medsystems, Inc. (Menlo Park, Calif.) focuses more precisely on space creation in the mediastinal cavity. However, the system provided is a mechanical lifting retractor with two sharply angled rotatable arms (14a, 14b) rather than a pneumatically inflatable assortment of curved balloons. Further, the method provided is aimed at creating a working space for cardiac surgery specifically by "temporarily expanding the space between the rib cage and the pericardium" and involves insertion between a pair of adjacent ribs (FIGS. 7-8 and Abstract). There is no mention of the trachea or bronchus.

Very few patents are directed specifically at instruments and methods for performing a mediastinoscopy as indicated by reference to "mediastinoscopy" in the claims. U.S. Pat. No. 7,473,530 (from hereon "USP '530") entitled "Method to detect lung cancer" by Maik Huttemann and assigned to Wayne State University (Detroit, Mich.) discloses methods of detecting cancer that involve comparing the levels of RNA for a specific component (COX4-2) in a first lung sample suspected to have cancer and a second lung sample known not to have cancer. The claims include a reference to "mediastinoscopy" along with several other possible diagnostic tests in the context of performing at least one additional test to confirm the lung cancer diagnosis based on the results of the first test comparing RNA (claim 20).

Similarly, there are relatively few United States patents referring to the "mediastinum" in the claims and of those that do almost all are directed at imaging methods, data analysis, or pharmaceutical treatment.

No patents can be found directly addressing atraumatic mechanical dilation of the mediastinal space.

With respect to the preferably toroidal design of the dilating element, U.S. Pat. No. 6,053,891 (from hereon "USP '891") entitled "Apparatus and methods for providing selectively adjustable blood flow through a vascular graft" teaches that the mediastinum is exposed in order to install a shunt by dividing the sternum. However, the patent is not directed at mediastinoscopy procedures. It cites to U.S. Pat. No. 3,730,186 (from hereon "USP '186") by Edmunds, et al. for disclosing the use of a "toroidal balloon" to occlude a native artery by placing the balloon around the outside of the artery. It teaches away from the use of a toroidal balloon because it is "believed to create crimps or infolds in the arterial wall even at low degrees of constriction" and "[s]uch crimps or infolds, which project into the flow field of the artery, are expected to disrupt laminar flow within the artery and serve as thrombogenic sites" (2:64-3:11). In the present invention this crimping problem would be avoided as the toroidal balloons herein are used inside conduits as dilators rather than outside conduits as occluders. Further, the toroidal balloons of the present invention are designed for use in larger conduits, canals, and cavities where they are not likely to be in the path of blood flow, rather than being used within or around the outsides of arteries and other blood vessels.

It would not be obvious to use toroidal balloons inside cavities and conduits as dilators including in the area alongside the trachea and in the pleural region. In the patent literature concerning medical devices and toroidal balloons they appear to be disclosed exclusively as occluders on the outside for preventing distal embolization around the heart. For example, see U.S. Pat. No. 7,458,980, U.S. Pat. No. 7,452,352, U.S. Pat. No. 7,396,329, U.S. Pat. No. 7,374,561, U.S. Pat. No. 7,335,192, etc.

None of the above patents provide systems, kits, or methods to dilate, easily sample, and improve visualization in the region outside the trachea during a mediastinoscopy procedure. Further, none of the above patents suggest accessing nodules on the outer trachea, bronchi, mediastinum, or lymph nodes without a neck incision by way of a natural orifice (including the mouth or nose) and natural lumens (including the throat and bronchi).

BRIEF SUMMARY OF THE INVENTION

The present invention provides a kit for performing a mediastinoscopy that improves access, sampling, and visualization. The various elements of the kit are designed to complement one another and be used together. However, any single element (i.e. the pieces for access only, sampling only, or visualization only) could also be used independently or with other commercially available products for mediastinoscopy or other procedures.

First, the access system includes expandable and collapseable elements for dilation extendable from the distal end of an instrument. These may take the form of inflatable balloons. More specifically, there may be one or more toroidal balloons having a hollow center region when expanded (similar to an inner tube flotation device used for the water sport "tubing" having the basic shape of a donut as but one example). The balloons can have any shape as long as they have a hollow center through which instruments can pass. When expanded, the toroidal ballons push against the inner walls of a channel in which they are inserted with their outermost outer surface (outside perimeter). They gently expand the channel and create a protected access and working zone (through their innermost outer surface or inside perimeter) for delivery and operation of instruments. Such instruments may include cameras, sampling and biopsy tools, needles, drug-delivery syringes, electrosurgical cutting and sealing tools, etc.

The toroidal balloons may be used for several purposes. One purpose is to expand a portion of the mediastinal cavity into which light from an endoscope may be directed for improved node visualization prior to grasping. Another purpose is to expand a difficult-to-reach portion of the mediastinal cavity, such as a crevice or narrow interstice between two adjacent structures, for easier access by grasping instruments to a node situated within the interstice. The toroidal balloons can also be used with other regular, non-toroidal balloons that block off an entire portion of the mediastinal cavity to protect sensitive structures or redirect flow, leaving unintended areas undisturbed as the sampling instrument (i.e. MEDIAGOPHER™ sampling instrument as discussed herein) goes after a target node. The atraumatic, flexible surface of an inflatable element such as a balloon provides minimal or no irritation to sensitive structures compared to what a grasping instrument with prongs or a cutting instrument with electrodes and/or blades would do.

Second, the sampling system of the present invention, the MEDIAGOPHER™ sampling instrument, includes a substantially circular head at the distal end 115 of an elongated body 101 with a small diameter and a low profile. The head has two jaws that form a mouth for "biting" samples. The "biting" process is used to cut/resect/separate tissue samples for biopsy or removal. The "biting" can be done with physically sharp elements (i.e. teeth, barbs, etc.) for mechanical cutting and/or electrodes for ablating, welding, and electrosurgically cutting, including combination teeth that are physically sharp and also electrically conductive to cut in more than one manner. The overall structure of the head and mouth assembly is similar to the PACMAN™ video game character in that it resembles a pizza or pie with a slice removed to form a mouth. The size of the missing slice can vary as the jaws open and close (increasing and decreasing the angle between them) to the extent necessary depending on the dimensions of the sample to be grasped and removed. The MEDIAGOPHER™ sampling instrument is termed a "gopher" because it burrows through the hollow spaces or holes in the center of the toroidal balloons after they are advanced and expanded. The MEDIAGOPHER™ sampling instrument waits for and follows the expanded toroidal balloons rather than being advanced before them so that it does not irritate the lumen through which it passes. In an alternative design, the toroidal dilating elements and the tissue resecting tool (MEDIAGOPHER™ sampling instrument) or another tool may work together such that a sensor on the unexpanded balloon detects the approaching tool and automatically expands in response thereto before the tool passes through it.

Third, the visualization system comprises a camera that provides a three hundred and sixty degree (360°) view positioned in the "throat" of the MEDIAGOPHER™ sampling instrument. The camera has a broad range of motion. Initially, it is positioned inside the small, narrow, elongated tube upon which the sampling jaw structure is mounted. In this position the camera is proximal to the sampler and the toroidal balloons. The camera can also be advanced to the region just between the sampling jaws for a direct close-up view of the sampling action. The camera can be advanced further beyond the MEDIAGOPHER™ sampling instrument and through more distal expanded toroidal balloons to explore an area before the MEDIAGOPHER™ sampling instrument jaws or other sampling instruments go there. The camera may also be advanced before balloons are advanced and expanded if it is unlikely to cause agitation. This on-site check keeps the sampler on track and confirms that the directions provided by any secondary navigation system (i.e. grid or coordinate system using ultrasound or X-ray data) are accurate. Optionally, communication between transmitters and receivers on the camera and already advanced balloons may be used to set-off expansion of the balloons just before or as the camera passes through them. By using the visualization system to explore a region before advancing other tools the trauma to the patient is minimized. Additionally, misalignment of the patient's body with a secondary navigation system can be quickly detected when the secondary system is instructing for the sampling instruments to move into an area in which there is no abnormal tissue, as seen by the on-site camera. Finally, according to a preferred embodiment, the 360° camera is also capable of doing a U-turn to look back upon the sampling jaws of the MEDIAGOPHER™ sampling instrument from a location distal to the sampling action to watch the biopsy process as it occurs from another perspective. This ability to do a U-turn compensates for any blind spot that may otherwise exist, even with "eyes in the back" and a 360° field of view, at a point where the instrument shaft attaches to the camera (for wiring, etc.).

Copending, commonly owned U.S. provisional application Ser. No. 61/090,510 entitled "Adaptable dilation system for mediastinoscopy and method of using" (filed Aug. 20, 2008) discloses the basic elements of the balloon dilation system. Copending, commonly owned U.S. provisional application Ser. No. 61/148,916 (filed Jan. 30, 2009) specifically discloses that the balloons can be toroids or donut-shaped with hollow spaces in the center through which instruments can pass.

The present invention provides a system and method to overcome the shortcomings in the reference art by focusing on the initial access phase of a mediastinoscopy procedure for lymph node sampling. The invention can be complementary or supplementary to existing mediastinoscopy tools by improving target visualization and access prior to the insertion of resecting tools with blades, electrodes, vacuums and compartmentalized collection chambers.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

For the access system the toroidal balloons can have any one of several shapes (including but not limited to donut, elliptical, oblong curved, irregularly curved, and polygonal) and sizes. The shape, size, and material of the balloons may be specially designed or selected depending on the shape, size, and other features of a canal, lumen, or cavity that must be dilated and through which other working instruments will be introduced. Therefore, the toroidal balloons can be chosen based on an individual's anatomy. The size of the toroidal balloons should be specially adapted to fit within the mediastinum including inside the trachea when deflated and outside the trachea when inflated. The shape, size, and material of the balloons can also be tailored to accommodate the working instruments themselves. The material and thickness chosen will influence the flexibility, strength, burst-resistance, maximum pressure, and other properties of the balloon. For example, smaller constricted passageways (trachea, bronchi, bronchioles, etc.) may need balloons of thicker or stronger material capable of withstanding greater pressure during the extent of dilation required to allow instruments to pass through them. Likewise, the balloons may be made thicker and from material with a higher resistance to bursting to accommodate bulkier instruments.

According to some embodiments, the balloons may be ribbed or textured on their surface to provide better traction (with less reliance on inflation) to stabilize them against adjacent structures.

The toroidal balloons may be deployed and activated (expanded or inflated) in any manner and to any extent that permits and facilitates the introduction of an instrument through them and reduces trauma to adjacent anatomical structures (i.e. the walls of a canal or cavity) without too much pressure from their expansion. Preferably, the balloons are deployed before the introduction of an instrument in order to dilate, expand and prepare a canal or cavity for receiving an instrument. According to one embodiment, the toroidal balloons may be deployed separately from an introducer instrument other than the instrument to be inserted through them. The introducer instrument can deploy and activate (expand) the balloons first before another sampling instrument is permitted to pass through them. The balloons can be attached to one another by string or wire and shot or propelled out of the distal end of an introducer instrument.

According to a second embodiment, the toroidal balloons may be directly connected to a cannula or directly connected to an instrument to be inserted through them. In this case the toroidal balloons may be deployed from the distal end and/or sidewalls of the cannula or instrument housing. Preferably, the cannula or instrument advances telescopically such that a balloon initially deployed from a distal tip becomes located at a sidewall as the remainder of the cannula/instrument is advanced through it and past it after expansion of the balloon. Before advancement and deployment the balloons may be stored in flaps on the outside walls of the instrument. Alternatively, balloons may be stored on the inside walls if there is a hole in the walls through which the balloons can pass to the outside, with the balloons themselves sealing the holes through which they are deployed.

The toroidal balloons absorb shock caused by manipulating instruments within them that would otherwise be absorbed by the inner walls of the lumen. By absorbing shock, the toroidal balloons reduce the sensation and soreness experienced by the patient. The balloons thereby permit a greater range of motion and force of pressure for the instruments while protecting the walls of bodily lumens and cavities from abrasion and irritation.

The present invention can be used with secondary navigation systems (other than primary navigation provided by direct on-site visualization via endoscopic camera or a surgeon's direct vision) such as those that map a coordinate grid on the body to identify and target nodes and then guide instruments in reaching them. Examples of such systems include those that incorporate ultrasound, X-rays, fluoroscopy, and/or radioactive isotopes to identify abnormal tissue and/or guide a surgeon to it. A problem with such systems is that they do not provide real-time identification or feedback. Identification and mapping typically precedes the sampling and if the body position moves or is disrupted during surgery the tracking will be off and the directions inaccurate. The camera of the present invention can be used to recognize these inaccuracies and re-establish a correspondence or tracking between the secondary navigation system and the body.

Alternatively, the 360° visualization provided by the camera of the present invention is powerful and comprehensive enough to be used alone to identify target sites for sampling without another secondary guidance system. To assist this process, one or more chemical compounds or dyes that are known to be selectively absorbed by abnormal tissue (i.e. via nanoparticle guidance or other means) can be administered in the vicinity of a target region preceding introduction of the camera. The camera that provides 360° visualization should be capable of providing this range of vision at any of several points along a trajectory extending from a region proximal to a target site, at the target site, and distally past a target site. Optionally, the camera may turn from side to side or even be capable of a complete U-turn to ensure a complete field of vision, including with backwards sight unobstructed by a "blind spot" at the point at which the extendable, bendable shaft attaches to the camera. This U-turn feature may be most useful after the camera has extended distally past the slit and the jaws, in order to look back at the slit and the jaws, such as to ensure target tissue has been effectively trapped by the jaws and, after removal, to ensure that no tissue remains caught in the jaws. The design of the jaws may include a canal therein that allows the camera shaft to remain extended through the jaws with the camera distal to the jaws while the jaws are closed. Preferably, the camera is configured to rotate about an axis along which it is extended and to articulate outside of the axis along which it is extended, including 180° U-turn articulation to look back upon the axis along which it is extended.

In its broadest form the visualization system of the present invention may be used in other surgical procedures as well and comprises a system configured to be advanced along a path from a region proximal to a target zone, through the target, to a region distal to the target zone, and to provide 360° of view from each position along the path. The target zone may be a cutting zone, a sealing zone, another type of treatment zone (such as where drugs are delivered), or a zone to be monitored.

With respect to the sampling system and the MEDIAGOPHER™ sampling instrument, the electrodes and/or physically sharp mechanical cutting elements can be integral with the jaws or formed from separate materials and embedded therein or mounted thereon. Although a two jaw PACMAN™ video game character style design is emphasized for simplicity, according to alternative embodiments, there may also be three or more pieces to the jaw structure that connect in the center when closed and open like a blossoming flower.

The access, sampling, and visualization systems of the present invention are designed to be used in modern minimally invasive surgical procedures, including endoscopic procedures and procedures that rely solely upon natural orifices for access (NOTES procedures: Natural Orifice Transluminal Endoscopic Surgery). When possible, accessing the mediastinum through the natural orifices and natural canals of the body (rather than cutting and carving out new openings and conduits) to the greatest extent practical is preferred. Avoiding external percutaneous incisions is especially preferred by patients for cosmetic reasons because it eliminates visible scars.

However, sometimes providing incisions in key locations can be advantageous to expand the range of sampling and/or improve visualization and perspective. For example, according to a preferred method of using the systems of the present invention, the instruments are inserted through the natural orifice of the mouth and then an incision is made through the trachea so that the instruments can freely move and collect samples along the outside of the trachea. This expands the range of sites that can be easily sampled. Conventional mediastinoscopy procedures involve an endotracheal tube with a small incision through the chest. These procedures can miss abnormal "exotracheal" tissue outside the trachea. It is easier to access the region outside the trachea along the way as instruments are introduced through the mouth rather than reversing direction after an incision through the chest thereby tearing up the chest to reach the outside of the trachea after an endotracheal entry.

In a preferred embodiment there is a plurality of toroidal balloons and each toroidal balloon is independently expandable and collapseable. This allows the surgeon greater control over the size and shape of the passageway created by toroidal balloon dilation. The toroidal balloons may be programmed to be inflated or collapsed sequentially, one after the next, or simultaneously all together at the same time. A combination of sequential and simultaneous inflation patterns may also be used in which the toroidal balloons within a group inflate/collapse simultaneously with respect to other toroidal balloons in the same group while the different groups of balloons inflate/collapse sequentially with respect to the other groups.

The toroidal balloons are preferably formed of an atraumatic biocompatible material including PEBAX™ block copolymer, nylon, polyester, polyvinylchloride (PVC), polyethylene terephthalate (PET), polyethylene (PE), or other materials, including combinations of any of the aforementioned materials. Different toroidal balloons may be made of different materials or of different amounts of materials (size and thickness) for different degrees of distensibility, maximum inflation pressure, volume, and/or diameter.

Different toroidal balloons can be made forwardly extendable to different degrees from the same reference point such as a distal tip of an insertion instrument. Preferably, each toroidal balloon is independently extendable and retractable. Preferably, each toroidal balloon may be steered or maneuvered radially about an axis and also turned/articulated (i.e. while extending longitudinally) at angles (to curve outside of and away from the axis of extension/advancement) to a central insertion axis after initial placement. These features permit navigation through tortuous pathways and around obstructions to allow for fine-tuning instrument position to hone in on a target sampling site.

The toroidal balloons may be used together with non-toroidal balloons without holes therein. The ordinary non-toroidal balloons can be inflated to an extent sufficient to seal off entire portions of the mediastinal cavity, thereby creating two or more distinct air and/or fluid tight compartments. These segregated compartments enable the use of gases for insufflation to collapse structures as needed to improve visualization. The compartments also make it safer and more efficient to aspirate or flush selected regions without over-broad application that risks redistributing particulates or drowning organs.

Figure 1:
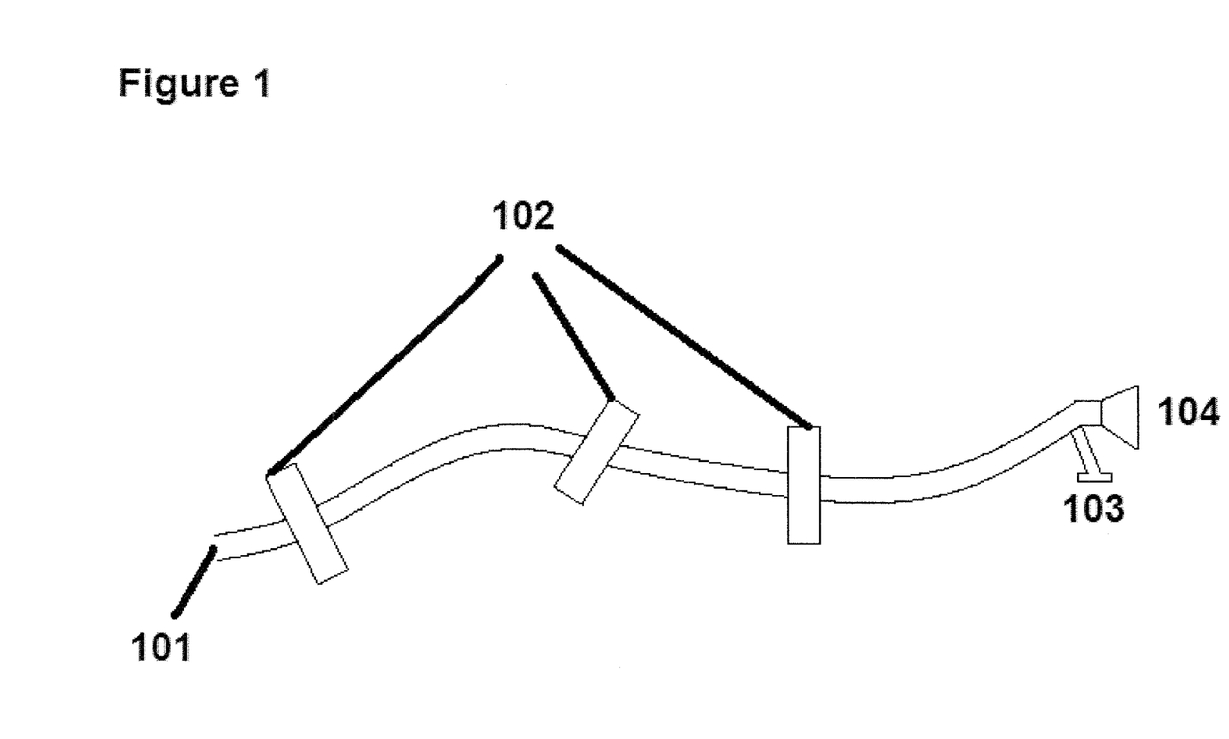
FIG. 1 is a side view of a generalized schematic representation of a multi-component dilation system of the present invention showing three expandable elements (balloons) spaced apart to dilate different regions outside of a working channel formed within a natural channel and enhanced with inflation from a proximal end of the dilation instrument.

FIG. 1 shows the basic features of the dilation system according to the present invention including a working channel 101, expandable elements (inflatable balloons) 102, a proximal port for an inflation system 103, and a proximal port for a visualization system 104.

Figure 2:
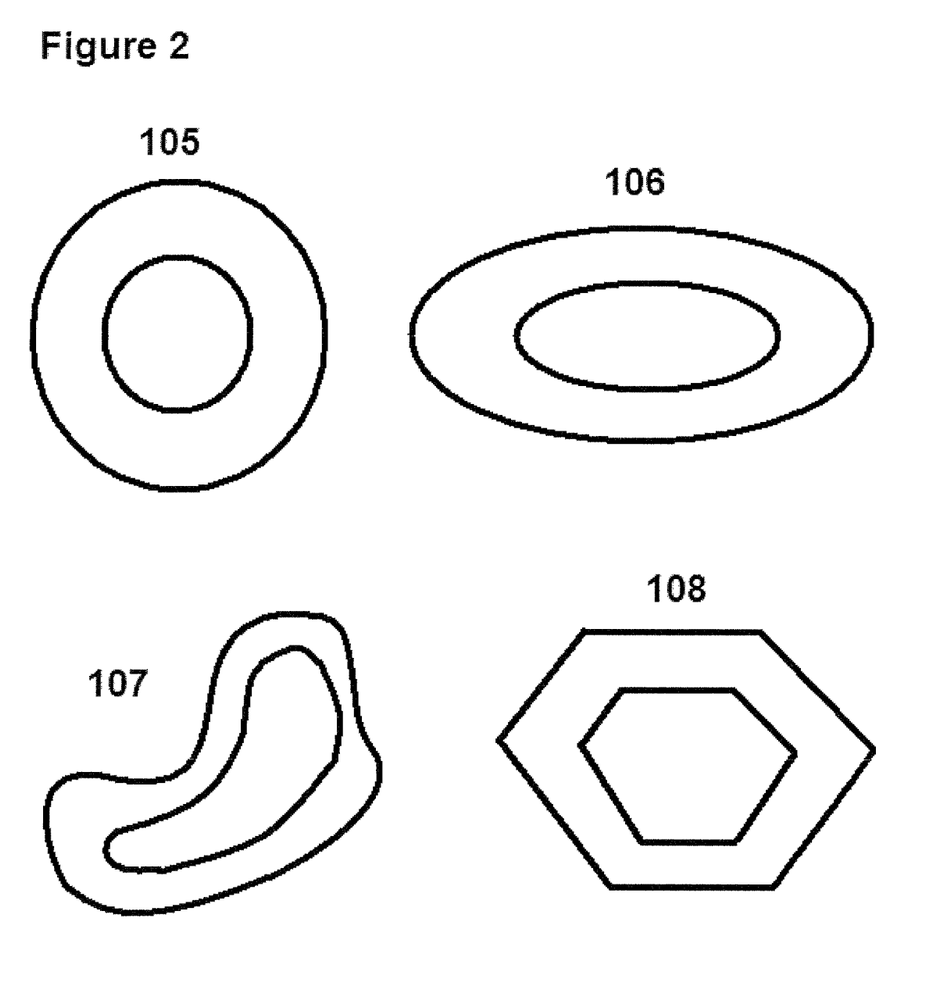
FIG. 2 illustrates cross-sections of the toroidal balloons of the present invention according to four different shapes of exemplary embodiments: (A) double circle or donut, (B) elliptical or oblong curved, (C) irregular curved, and (D) polygon.

FIG. 2 shows four exemplary embodiments for the shape of the expandable elements 102. Among other options, they may be: donut-shaped toroid 105 with both inner and outer perimeters circular; elliptical or oblong curved toroid 106 with both inner and outer perimeters curved but not circular; irregularly curved toroid 107 with both inner and outer perimeters curved and in which inner and outer perimeters may or may not be completely symmetrical such that the thickness or volume of inflated space between them may or may not be uniform around the perimeter; and polygonal toroid 108 with sharper angles at turns rather than smooth curves (alternatively and not shown, a sharp-angled toroid need not a be a regular polygon but may also be any irregular enclosed form).

Figure 3:
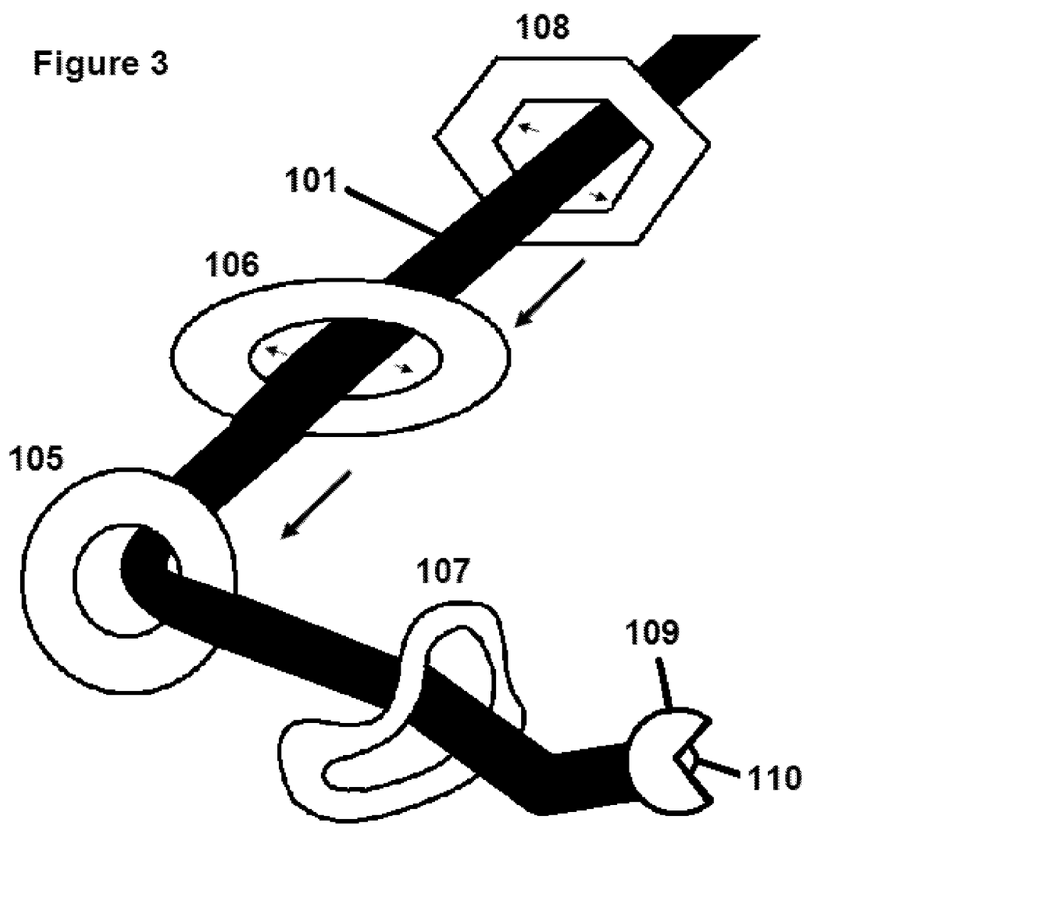
FIG. 3 illustrates several exemplary toroidal balloons of the present invention deployed alongside a working channel to expand against and retract sidewall tissue in order to create a working channel through their centers in which an instrument can freely operate with reduced trauma.

FIG. 3 shows some of the different types 105-108 of expandable elements 102 as in FIG. 2, with the working channel 101 worming through them. The individual ports through which each expandable element may be individually inflated through an inflation pipe in the working channel are not shown. At a distal end 115 of the working channel 101 are the sampling jaws 109 of the MEDIAGOPHER™ sampling instrument and a camera 110 at the distal end of the visualization system. Elongated shafts upon which both the sampling jaws 109 and camera no are mounted may be housed within the working channel 101 and are not shown (i.e. see camera shaft in shown in FIG. 4).

The distal end of the sampling instrument has a mouth that resembles the PACMAN™ video game character (circular shape like a pie or pizza but with one or more slices missing from a single region) with two or more jaws 109 having cutting elements thereon for grasping and resecting tissue. The distal end also includes a spherical camera 110 to provide 360° visualization.

Figure 4:
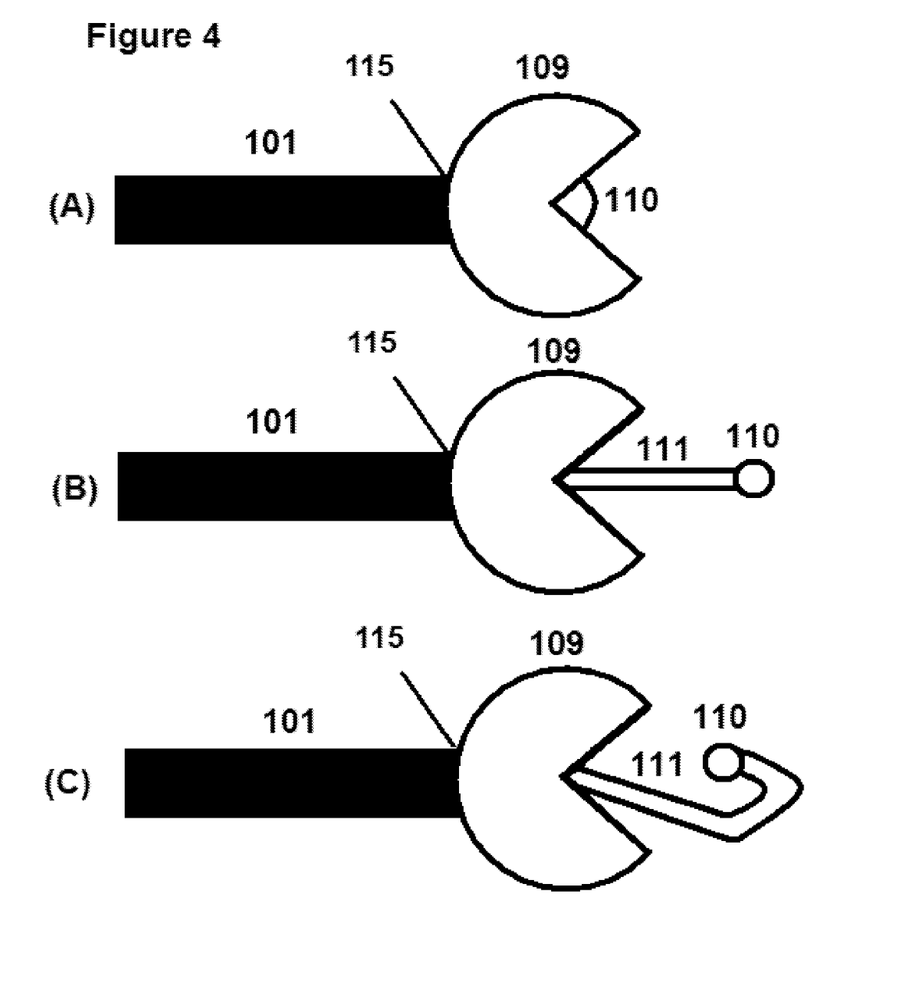
FIG. 4 illustrates a distal end of a sampling resecting instrument according to the present invention.

FIG. 4 shows the camera 110 in three different positions relative to the sampling jaws 109. In (A) the camera 110 is just beginning to protrude through the jaws 109. In (B) the camera 110 has been moved distally past the jaws 109 by extension of the shaft 111 upon which it is mounted through the working channel 101. In (C) the extendable shaft 111, upon which the camera 110 is mounted, has been bended such that the camera 110 is turned 180° from its original position to look back upon the jaws 109.

Figure 5:
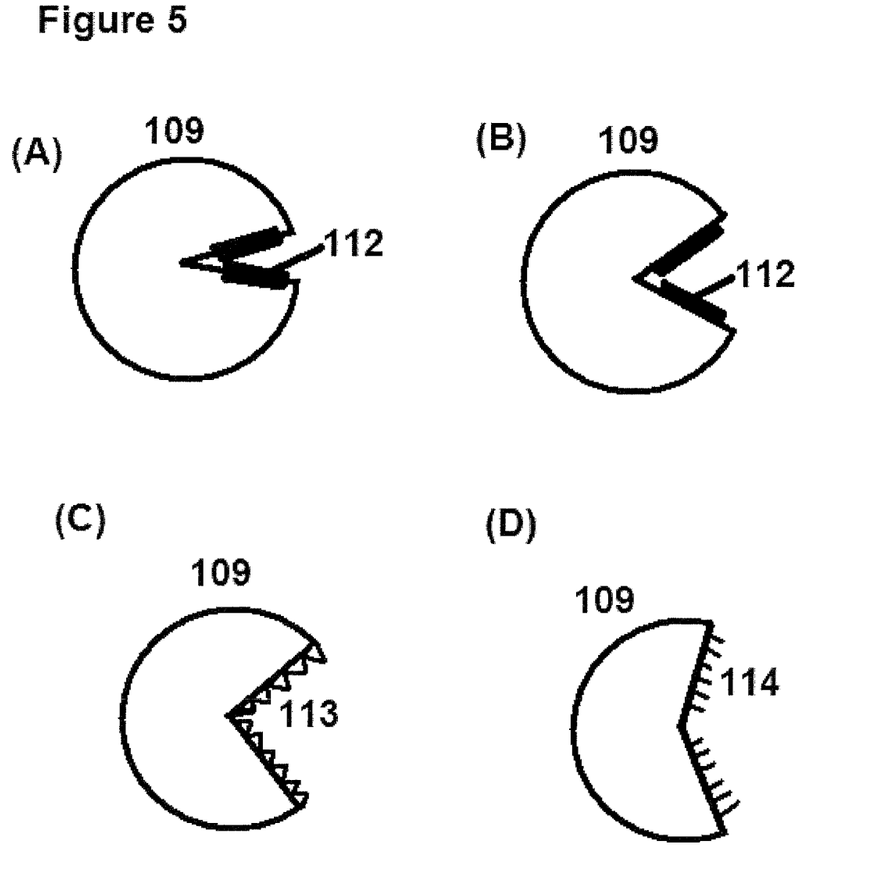
FIG. 5 illustrates various exemplary embodiments and positions for a mouth with two jaws having cutting elements thereon to resect and detach tissue to be treated or sampled. The mouth may open to different degrees from slightly (A) to severely (D) with physically sharp and/or electrically conductive elements thereon for mechanical and/or ablative cutting and/or sealing.

FIG. 5 shows the sampling jaws 109 with three different alternative types of cutting elements for severing tissue. Also, from (A) to (D) the jaws progressively move from a near completely closed position in (A) to a near completely open position in (D) as needed to receive a target (i.e. tissue, lymph nodes, etc.). In (A) and (B) the cutting elements are electrodes 112 which may also be used for sealing in addition to cutting before, during, or after cutting. Sealing assists with hemostasis. In (A) the electrodes 112 are embedded within the mouth of the jaws and in (B) the electrodes 112 are mounted on the surface inside the mouth. In (C) the cutting elements are physically sharp triangular teeth 113 that cut mechanically and may or may not also be electrically conductive for ablation. In (D) the cutting elements are physically sharp barbs 114 that cut mechanically and may or may not also be electrically conductive for ablation. Alternatively, separate electrode elements may be incorporated upon or within the sharp mechanical cutting elements or the sharp elements may be mounted upon or within the electrodes for a multifaceted (electrical and mechanical) approach to resecting and/or sealing.

The present invention is not limited to the embodiments described above. Various changes and modifications can, of course, be made, without departing from the scope and spirit of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A device, capable of insertion into an exotracheal tissue region, the device including:
    an elongated body having an axis, a distal end ending in a distal tip, and a lumen extending through the elongated body, the lumen ending in an opening at the distal tip;
    at least three expandable elements coupled to the distal end of the elongated body, the at least three expandable elements configured to access and dilate a passageway within the tissue region,
    wherein each one of the at least three set of expandable elements defines a corresponding one of a plurality of openings between an inner diameter of the respective expandable element and an external surface of the elongated body, such that the plurality of openings provide access to the tissue region along the axis of the elongated body.

2. The device of claim 1,
    wherein each of the at least three expandable elements includes a respective one of a plurality of toroidal balloons, the inner diameter of each of the plurality of toroidal balloons, when expanded, being substantially greater than an outer diameter of the elongated body.

3. The device of claim 1, further including:
    a substantially circular element provided at the distal end of the elongated body, the circular element including first and second jaws, each having a cutting element.

4. The device of claim 1, wherein each of the at least three expandable elements includes a surface having ribbing or texture.

5. The device of claim 1, wherein the at least three expandable elements is configured to absorb shock from instruments within the passageway.

6. The device of claim 1, wherein the at least three expandable elements includes three toroidal balloons.

7. A system, comprising:
   at least three expandable toroidal balloons, each of the at least three expandable toroidal balloons being disposed for expansion from an axis of an elongated body insertable into a patient's body from a region external to the patient's body, each one of the at least three plurality of expandable toroidal balloons being spaced a corresponding one of a plurality of distances along the axis of the elongated body from adjacent ones of the at least three expandable toroidal balloons,
   wherein each one of the at least three expandable toroidal balloons defines a corresponding one of a plurality of openings between an inner diameter of the respective expandable toroidal balloon and an external surface of the elongated body, such that the plurality of openings provide access to the tissue region along the axis of the elongated body,
   wherein the elongated body includes a distal tip, and a lumen extending through the elongated body, the lumen ending in an opening at the distal tip.

8. The system of claim 7, wherein the at least three expandable toroidal balloons includes three toroidal balloons.

9. The system of claim 7, wherein the at least three toroidal balloons are configured to be positioned at one or more locations within the body prior to expansion.

10. The system of claim 9, wherein the at least three toroidal balloons are extendable from a distal end of an introducer instrument.

11. A method of using the access system of claim 10,
    wherein each toroidal balloon positioned proximally (closer to a site of introduction) to another balloon is expanded before the other balloon more distal to it, such that after expansion of the more proximal balloon the other balloon can be easily passed through it and then itself expanded, whereby the balloons expand in a proximal to distal domino manner with a most proximal balloon as first to expand and a most distal balloon as last to expand.

\* \* \* \* \*